United States Patent [19]

Randhawa

[11] 4,232,225
[45] Nov. 4, 1980

[54] CHEMILUMINESCENT METHOD AND APPARATUS FOR THE DETECTION OF OZONE

[75] Inventor: Jagir S. Randhawa, Las Cruces, N. Mex.

[73] Assignee: The United States of America as represented by the Secretary of the Army, Washington, D.C.

[21] Appl. No.: 4,625

[22] Filed: Jan. 19, 1979

[51] Int. Cl.$^3$ ............................................. G01T 1/20
[52] U.S. Cl. ................................ 250/361 C; 250/435
[58] Field of Search ........................... 73/170 R, 189; 250/361 C, 435; 244/3.1

[56] References Cited

U.S. PATENT DOCUMENTS

| | | | |
|---|---|---|---|
| 2,939,127 | 5/1960 | Graw | 73/170 R |
| 3,688,115 | 8/1972 | Antkiw | 250/269 |
| 3,724,956 | 4/1973 | Neary | 250/361 C |
| 3,726,599 | 4/1973 | Neary | 250/361 C |
| 3,995,558 | 12/1976 | Travor et al. | 244/3.1 |

*Primary Examiner*—Alfred E. Smith
*Assistant Examiner*—Carolyn E. Fields
*Attorney, Agent, or Firm*—Nathan Edelberg; Jeremiah G. Murray; Edward Goldberg

[57] ABSTRACT

Ozone may be detected in the upper atmosphere by the ozonesonde of the subject invention. The inventive ozonesonde directs an ambient air flow in a continuous stream over a chemiluminescent disc, which reacts with the ozone to produce oxygen and light. The intensity of the light is detected and measured as an indicator of the ozone concentration. The air flow is exited from the instrument thereby allowing a maximum quantity of air to be sampled for a more accurate determination of the oxygen concentration.

7 Claims, 4 Drawing Figures

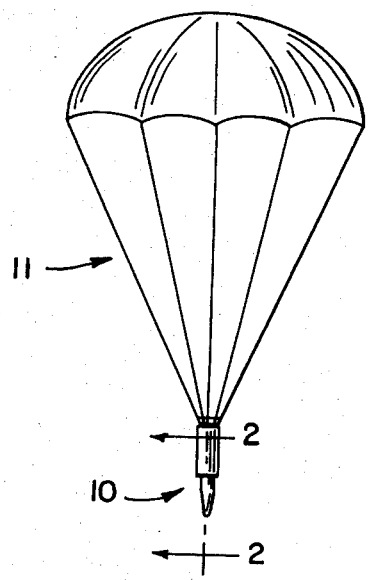
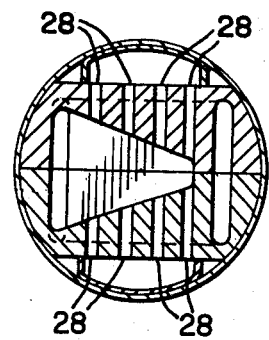
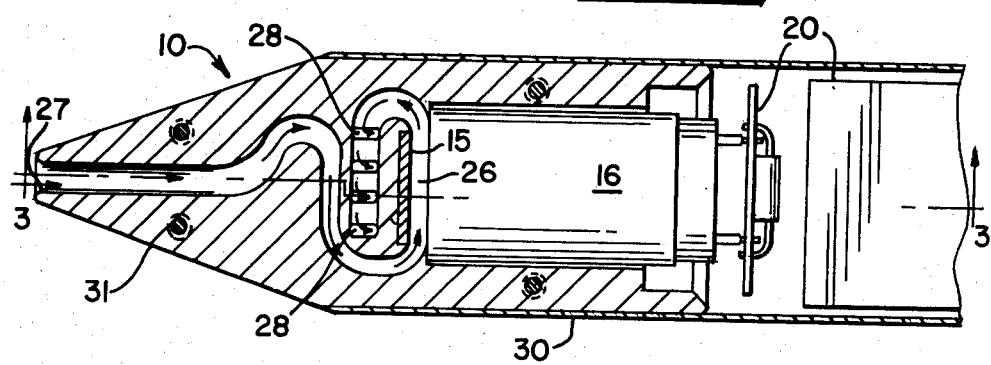
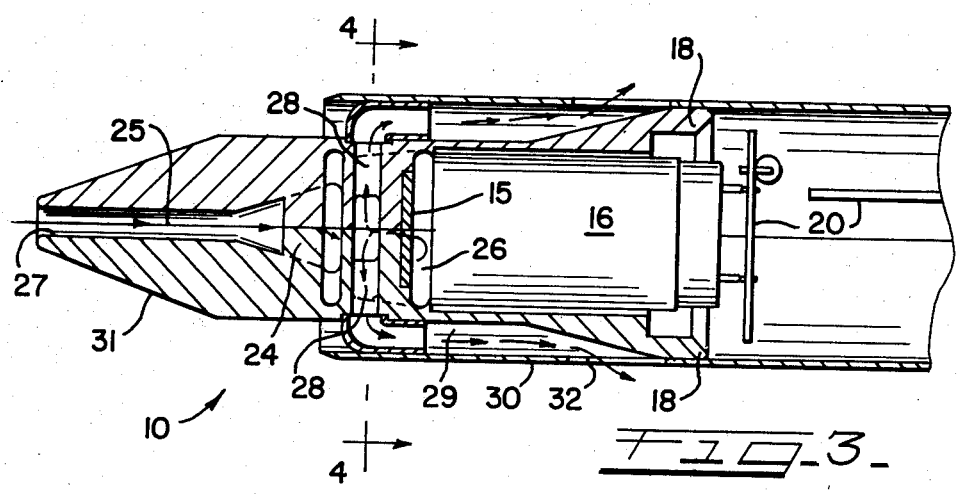

CHEMILUMINESCENT METHOD AND APPARATUS FOR THE DETECTION OF OZONE

BACKGROUND OF THE INVENTION

This invention relates to a chemiluminescent detection apparatus and, more particularly, to a chemiluminescent detection apparatus which is capable of detecting and measuring the presence and concentration of ozone or other oxidant material in the upper atmosphere.

Because of efforts being undertaken to reduce atmospheric pollution, reliable methods are needed for monitoring the level of various individual noxious gases in the ambient atmosphere resulting from various effluent sources, such as vehicle exhausts, factory emissions and the like. The detection of the presence of pollutants in sub part per million levels by the observation of chemiluminescent reaction is particularly attractive because the method can be adapted to be continuous and because long path length observation is not required as in absorption spectroscopy. A chemiluminescent reaction occurs where a primary reactant, such as ozone, engages in a highly exothermic reaction with certain second reactants or reagents to emit radiant energy, usually in the infrared region. Sensitive detectors can be calibrated to respond to the chemiluminescent emission in direct proportion to the concentration of the primary or desired reactants in the sample being studied. Examples of such chemiluminescent detectors are taught in U.S. Pat. Nos. 3,271,113; 3,848,128; 3,984,688; 3,710,107 and 3,528,779.

Ozone in the upper atmosphere has been measured in the past by a rocket-borne ozonesonde which directly measures ozone concentration in a continuous manner, thereby yielding data showing the partial pressure of ozone as a function of altitude. However, these prior art ozonesondes relied on pressure differentials between the upper and the lower atmospheres to provide for a flow of the ozone over the detector and do not provide for a sampling of a large volume of air on a continuous basis.

SUMMARY OF THE INVENTION

Accordingly, an object of the subject invention is the provision of a chemiluminescent detection apparatus which may be used to continuously and accurately detect the presence and concentration of ozone in the upper atmosphere.

Another object of the subject invention is the provision of a maximum flow rate through the sensor sampling chamber by maximizing the pressure difference across the sampling chamber.

These and other objects are attained in accordance with the present invention wherein there is provided an ozonesonde instrument having an aerodynamic sampling head, a chemiluminescent sensor disc, a photomultiplier tube and telemetric circuitry. The ozonesonde has a housing in the shape of a rocket or cylinder with a frustoconically-shaped leading edge. The leading edge or nose of the instrument may be weighted relative to the rest of the apparatus assuring that the nose will always be pointed in a downward direction during sampling operations. An intake orifice is located at the leading edge and directs the onrushing air through a baffle channel or duct which directs the air across a sensing disc of chemiluminescent material, with which the ozone reacts to form molecular oxygen and light. The air flow is then directed through the channel and out a light baffled exit duct into a low pressure region of atmosphere surrounding the instrument.

DESCRIPTION OF THE DRAWINGS

These and other objects, advantages and features will become apparent from the detailed description below, taken in conjunction with the accompanying drawings wherein like reference characters refer to like parts throughout and in which:

FIG. 1 is a perspective view of the ozonesonde of the subject invention in a sampling operation and descending by parachute;

FIG. 2 is a cross-sectional view of the ozonesonde of the subject invention;

FIG. 3 is a cross-sectional view of the ozonesonde of the subject invention taken along the lines 3—3 of FIG. 1;

FIG. 4 is a cross-section taken along the lines 4—4 of FIG. 3, showing the exit ducts.

Referring now to FIG. 1, there is shown an ozonesonde 10 descending from the upper atmosphere by means of a parachute 11 in a typical sampling operation. The ozonesonde 10 may be deployed to such as altitude by a rocket (not shown) and released to allow the parachute 11 to open for a controlled descent. The ozonesonde 10 of the subject invention, as shown in FIG. 2, has a main body 30 and a frustoconical leading end portion 31. In the interior of the main body 30 of the ozonesonde of the subject invention, the instrument includes a photomultiplier tube 16 of known type anchored securely within the housing 31 by mounts 18 or the like. The photomultiplier tube monitors or detects the destruction of the ozone molecules on the chemiluminescent material disc 15 and generates a signal in direct proportion to the intensity of the light emitted in such destruction. As is well known, the passage of the atmospheric ozone across the disc, which is formed of suitable chemiluminescent material, cause a reaction to generate molecular oxygen and light. The intensity of the light generated by this reaction is directly proportional to the concentration of ozone in the atmosphere. Therefore, detection of the light and measurement of its intensity by the photomultiplier tube 16 comprises a direct measurement of the concentration of ozone in the atmosphere.

The photomultiplier tube 16 is connected to solid state circuitry such as circuit boards 20, comprising a telemetry system for transmitting the measured signal or output of the photomultiplier tube to a suitable receiver on the ground for visual display of the generated signal.

As described above, prior art rocket ozonesonde instruments utilized an internal ballast chamber which produced reasonable flow rates as a result of the differential pressure experienced between external atmosphere and the ballast chamber. With such a device the air sample flow rate was determined largely by the ballast chamber size and the instrument descent rate. Since a larger ballast chamber produced a larger flow rate, relatively large instruments were necessary.

With the ozonesonde of the subject invention, a ballast chamber is rendered unnecessary, thereby allowing further miniaturization of the instrument in accordance with the state of the art in electronics. In addition, the reaction chamber size may be smaller, since the air flow rate will be proportionately larger.

The nose section 31 of the ozonesonde of the subject invention which is frustoconical in shape for greater aerodynamic stability incorporates a front orifice 27 for accepting the air flow 25 generated by the rapid descent of the instrument 10. The air flow 25 enters the nose portion 31 of the instrument and is forced to conform to the channels or ducts 24 which direct the air flow through the instrument. This forces the air flow 25 into at least two ninety degree turns prior to passing through the reaction area or chamber 26 between the photomultiplier tube 16 and the chemiluminescent disc 15. In this reaction area or chamber 26, the continuous flow of the air causes the ozone in the air to react with the chemiluminescent disc to emit light, as described above, in direct proportion to the concentration of ozone within the air flow 25. The emission of this light by the ozone is sensed by the photomultiplier tube which emits a signal for transmission to an appropriate receiving station. The air flow continues on its way forced through a triangular exit chamber and into another series of ninety degree turns out of a series of exit ducts 28. The air flow is continuous at all times when the ozonesonde 10 is descending.

As shown in FIGS. 3 and 4, the air flow 25 exits from ducts 28 into channel 29 underneath the outer housing 30 out opening 32, and returns to the atmosphere 35 in the low pressure region immediately surrounding the instrument body 30, thereby causing a maximum air flow into the reaction chamber. As shown in FIGS. 3 and 4, the air flow is divided equally to exhaust from opposite sides of the ozonesonde, thereby maintaining equilibrium of the instrument. The ducts 24 and 28 for the flow of air 25 through the ozonesonde 10, may be formed of or coated with Teflon which eliminates the collection of film or coating contaminants that may be inducted with the atmospheric gases, to thereby increase the longevity of the reaction chamber 26. Such a material will thereby permit maximum efficiency in light collection for detection over an extended period of time.

The ducts 24 and 28 also provide for at least two ninety degree turns for air flow 25 prior to reaching the reaction area 26 and prior to exiting from the ozonesonde after leaving the reaction area 26. Such turns eliminate stray light which would interfere with the accurate reading of light emission within the reaction area 26.

In operation, the ozonesonde may be deployed by a rocket into the stratopause where a parachute 11 as depicted in FIG. 1 will guide and control its rate of descent. Gases flow through the orifice 27 into the channel 24 as the instrument descends on a radar reflecting parachute 15 feet in diameter. The air flow passes through channel 24 across the chemiluminescent sensing disc 15 as it passes through the reaction chamber 26. The ozone in the environment reacts with the chemiluminescent material in the disc 15 producing molecular oxygen and photons, or light, which is detected by the photomultiplier tube 16. The photomultiplier tube 16 emits an output signal which is transmitted to the appropriate receiving station for visual display and recording. By the above-described structure, the pressure difference across the sampling chamber is maximized, the flow rate being substantially dependent upon the dynamic pressure due to the instrument descent rate and the sensor resistance to flow. The concentration of ozone may be easily determined, since the altitude and rate of descent of the instrument may be known through radar tracking. The net flow of air through the instrument depends largely on the size of the orifice 27 and the rate of descent. Knowing these parameters, the ozone concentration may be calculated for any given altitude and may be accurately computed and graphed as a function of altitude as a result of the continuous sampling of the large volumes of air.

The ozonesonde is calibrated before launch by the use of an ozone generator of standard design. Ozonized air of known concentration is injected into the ducts 24 past the chemiluminescent disc 15 at a known flow rate and sensitivity is set in the proper range.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

I claim:

1. An apparatus for the continuous detection and measurement of ozone in the atmosphere as a function of altitude, said apparatus comprising a main body portion and a nose portion, said main body portion housing a reaction chamber, detector and amplifying means for generating a signal proportional to the concentration of ozone in said reaction chamber, a body of ozone reactive chemiluminescent material in said reaction chamber, a transmitter means for transmitting said signal, said nose portion being frustoconical for aerodynamic stability and having an opening communicating with a duct for the admission of an ambient air flow through said opening into said duct, said air flow occurring as said apparatus falls through said atmosphere, said duct excluding stray light and directing said air flow into said reaction chamber over and in contact with said body of chemiluminescent material, the ozone in said air flow reacting with said chemiluminescent material to form molecular oxygen and emit light, said air flow being directed in a continuous stream through said reaction chamber into at least one exit duct and an exit chamber, said exit duct excluding stray light from said reaction chamber, said exit chamber including a pair of openings on opposite sides directing said air flow equally through said openings out of said apparatus to maintain equilibrium, the light emitted by the reaction of said ozone with said chemiluminescent material being proportional to the concentration of ozone in said air flow and being detected by said detector and amplifying means, the signal generated by said detector and amplifying means being transmitted to a receiver for visual display.

2. The apparatus of claim 1 wherein said opening is formed at the front face of said frustoconical nose portion.

3. The apparatus of claim 1 wherein said exit chamber is triangular.

4. The apparatus of claim 1 wherein said exit chamber directs said air flow out of said apparatus into a low pressure region immediately surrounding said apparatus during said fall and causing a maximum air flow through said apparatus.

5. A method for continuously measuring the concentration of ozone in the atmosphere by chemiluminescence as a function of altitude, comprising the steps of:
(1) conveying a detection apparatus to the upper atmosphere;
(2) causing said detection apparatus to descend in the atmosphere in a controlled manner to establish a flow of air through said apparatus;
(3) directing a continuous stream of said air within said detection apparatus and through a duct having at least two ninety degree turns to exclude stray light;
(4) directing said air through a reaction chamber within said detection apparatus over a body of ozone reactive chemiluminescent material in said chamber;
(5) reacting the ozone in said air with said chemiluminescent material to produce molecular oxygen and light in proportion to the concentration of ozone in said air;
(6) detecting said light and generating a signal directly proportional to the intensity of said light;
(7) transmitting said signal to a receiver for visual display;
(8) and exhausting said air flow through an exit duct excluding stray light from said reaction chamber and an exit chamber having opposing openings directing said air in a continuous evenly distributed manner out of both sides of said detection apparatus in an area of low pressure immediately adjacent said detection apparatus.

6. The method of claim 5 further including the steps of:
(1) determining the altitude and rate of descent of said apparatus;
(2) determining the net flow of air through said apparatus; and,
(3) determining the concentration of ozone in the atmosphere at a given altitude.

7. An apparatus for the continuous detection and measurement of ozone in the atmosphere as a function of altitude, said apparatus comprising an outer cylindrical body portion and a nose portion, said outer body portion housing a reaction chamber, detector and amplifier means for generating a signal proportional to the intensity of light in said reaction chamber, a body of ozone reactive chemiluminescent material in said reaction chamber and a transmitter means for transmitting said signal, said nose portion being frustoconical for aerodynamic stability with a central opening communicating with a duct for the admission of an ambient air flow through said opening into said duct, said air flow occurring as said apparatus falls through said atmosphere, said duct having at least two right angle turns prior to said reaction chamber to exclude stray light and directing said air flow into said reaction chamber over and in contact with said body of chemiluminescent material, the ozone in said air flow reacting with said chemiluminescent material to form molecular oxygen and emit light, said air flow being directed in a continuous stream through said reaction chamber into a pair of exit ducts having right angle turns to exclude stray light and an exit chamber, said exit chamber having a pair of openings, on opposing sides, each of said openings directing said air flow equally out of said apparatus to maintain equilibrium of said apparatus, the light emitted by the reaction of said ozone with said chemiluminescent material being proportional to the concentration of ozone in said air flow and being detected by said detector and amplifying means, the signal generated by said detector and amplifying means being transmitted to a receiver for visual display.

* * * * *